United States Patent
Subramaniyam

(10) Patent No.: US 9,334,445 B2
(45) Date of Patent: May 10, 2016

(54) AMINE BASED ADDITIVE COMPOSITION FOR CONTROL AND INHIBITION OF POLYMERIZATION OF STYRENE, AND METHOD OF USE THEREOF

(71) Applicant: Dorf Ketal Chemicals (India) Private Limited, Mumbai (IN)

(72) Inventor: Mahesh Subramaniyam, Mumbai (IN)

(73) Assignee: Dorf Ketal Chemicals (India) Private Limited, Mumbai (IN)

( * ) Notice: Subject to any disclaimer, the term of this patent is extended or adjusted under 35 U.S.C. 154(b) by 0 days.

(21) Appl. No.: 14/361,220

(22) PCT Filed: Nov. 16, 2012

(86) PCT No.: PCT/IN2012/000751
§ 371 (c)(1),
(2) Date: May 28, 2014

(87) PCT Pub. No.: WO2013/098846
PCT Pub. Date: Jul. 4, 2013

(65) Prior Publication Data
US 2014/0316172 A1      Oct. 23, 2014

(30) Foreign Application Priority Data
Nov. 29, 2011   (IN) .......................... 3350/MUM/2011

(51) Int. Cl.
C07C 7/20 (2006.01)
C09K 15/20 (2006.01)
C07B 63/04 (2006.01)

(52) U.S. Cl.
CPC .................. C09K 15/20 (2013.01); C07B 63/04 (2013.01); C07C 7/20 (2013.01)

(58) Field of Classification Search
USPC .................. 585/2, 3, 4, 5, 406, 428
See application file for complete search history.

(56) References Cited

U.S. PATENT DOCUMENTS

| | | | |
|---|---|---|---|
| 5,254,760 A | 10/1993 | Winter et al. | |
| 5,290,888 A * | 3/1994 | Gatechair et al. | 526/83 |
| 5,488,192 A * | 1/1996 | Kourbatov et al. | 585/435 |
| 5,545,786 A * | 8/1996 | Winter et al. | 585/435 |
| 5,744,672 A * | 4/1998 | Kourbatov et al. | 585/440 |
| 6,117,276 A * | 9/2000 | Cunkle et al. | 203/8 |
| 6,284,936 B2 * | 9/2001 | Shahid | 585/4 |
| 6,395,942 B1 * | 5/2002 | Kurek et al. | 585/5 |
| 6,395,943 B1 * | 5/2002 | Kurek et al. | 585/5 |
| 6,403,850 B1 | 6/2002 | Benage et al. | |
| 6,409,887 B1 * | 6/2002 | Pryce et al. | 203/9 |
| 6,660,181 B2 * | 12/2003 | Benage et al. | 252/183.12 |
| 6,673,879 B2 * | 1/2004 | Shahid | 526/82 |
| 6,899,806 B2 | 5/2005 | Benage et al. | |
| 7,045,647 B2 * | 5/2006 | Benage | 560/4 |
| 7,943,809 B2 * | 5/2011 | Benage et al. | 585/5 |
| 8,013,083 B2 | 9/2011 | Kosover et al. | |
| 8,691,994 B2 * | 4/2014 | Tong | 546/248 |
| 8,766,027 B1 * | 7/2014 | Subramaniyam | 585/428 |
| 2004/0104146 A1 | 6/2004 | Benage et al. | |
| 2006/0178489 A1 | 8/2006 | Kosover et al. | |
| 2009/0240092 A1 * | 9/2009 | Ma et al. | 585/5 |

FOREIGN PATENT DOCUMENTS

| | | |
|---|---|---|
| IN | 3350MUM2011 | 11/2011 |
| WO | 2013098846 A1 | 7/2013 |
| WO | 2013098846 A4 | 7/2013 |
| WO | 2013098846 A8 | 7/2013 |

OTHER PUBLICATIONS

Foreign communication from the priority application—International Search Report and Written Opinion, PCT/IN2012/000751, Jun. 4, 2013, 9 pages.

* cited by examiner

*Primary Examiner* — Ellen McAvoy
(74) *Attorney, Agent, or Firm* — Conley Rose, P.C.; Rodney B. Carroll

(57) ABSTRACT

The present invention relates to amine based additive composition for controlling and inhibition of polymerization of aromatic vinyl monomers including styrene comprising (a) one or more of nitroxide (i.e. nitroxyl) compounds; and (b) one or more of aromatic nitro compounds, characterized in that the said composition further comprises one or more of (c) amines, wherein said amine is selected from a group comprising (i) hydroxyl alkyl tertiary amines, (ii) tertiary alkyl amines, (iii) hydroxyl alkyl primary amine; and (iv) mixture thereof. In one embodiment, the present invention also relates to method of using presently provided composition. In another embodiment, the present invention also relates to method of controlling and inhibiting polymerization of aromatic vinyl monomers including styrene by employing presently provided composition. In still another embodiment, the present invention also relates to method of preparation of presently provided composition.

20 Claims, No Drawings

AMINE BASED ADDITIVE COMPOSITION FOR CONTROL AND INHIBITION OF POLYMERIZATION OF STYRENE, AND METHOD OF USE THEREOF

CROSS-REFERENCE TO RELATED APPLICATIONS

This application is a filing under 35 U.S.C. 371 of International Application No. PCT/IN2012/000751 filed Nov. 16, 2012, entitled "Amine Based Additive Composition for Control and Inhibition of Polymerization of Styrene, and Method of Use Thereof," which claims priority to Indian Patent Application No. 3350/MUM/2011 filed Nov. 29, 2011, which applications are incorporated by reference herein in their entirety.

FIELD OF THE INVENTION

The present invention relates to amine based additive composition for control and inhibition of polymerization of aromatic vinyl monomers, wherein aromatic vinyl monomers include styrene.

In one embodiment, the present invention relates to method of using amine based additive composition to control and inhibit polymerization of aromatic vinyl monomers including styrene.

In another embodiment, the present invention relates to method of preparation of amine based additive composition for control and inhibition of polymerization of aromatic vinyl monomers including styrene.

In still another embodiment, the present invention relates to method of controlling and inhibiting polymerization of aromatic vinyl monomers including styrene by employing amine based additive composition.

BACKGROUND OF THE INVENTION

The polymerization of aromatic vinyl monomers including styrene during processing is a matter of concern, because it causes formation of unwanted polymers and results in loss of yield of end product and makes the process un-economical.

In the art use of inhibitors and retarders, and combination thereof to overcome problem of polymerization of aromatic vinyl monomers including styrene has been reported.

The problem of using the inhibitors alone is that these are to be added continuously or at regular interval, because once they are consumed, the polymerization will re-start.

The problem of using the retarders alone is that these are not very effective to reduce polymerization of aromatic vinyl monomers including styrene to a level of substantial inhibition or to the acceptable level of inhibition.

The prior art [U.S. Pat. No. 5,254,760 (US' 760)] discloses the polymerization inhibition of vinyl monomers using a combination of nitroxides (i.e. nitroxyl compounds) including 1 oxyl-2,2,6,6,tetramethylpiperidin-4-ol (4HT) and aromatic nitro compounds including dinitro-butylphenol [re abstract, Col. 3, lines 26-32; Col. 4, lines 1-2, 12] as the polymerization inhibitor. However, the aromatic nitro compounds including DNBP are to be used in higher amounts and/or are also known for their toxic nature for human exposure [re Col. 1, lines 64-68].

Therefore, the industry is aiming for additive composition wherein the dosage of components of composition of US' 760, particularly of DNBP and 4HT can be minimized or reduced. Any effort in the direction of lowering the consumption of these components will lessen the problem of industry.

NEED OF THE INVENTION

Therefore, there is still a need of an effective additive composition and method of its use, and method of its preparation and method of controlling and inhibiting polymerization of aromatic vinyl monomers including styrene by employing said composition, wherein the additive composition is not only suitable for substantial control and inhibition of polymerization of aromatic vinyl monomers including styrene, but also comprises reduced or minimized amounts of nitroxides (i.e. nitroxyls) and aromatic nitro compounds.

SUMMARY OF THE INVENTION

Therefore, the present invention aims at providing a solution to above-described existing industrial problem by providing effective additive composition and method of its use, and method of its preparation and method of controlling and inhibiting polymerization of aromatic vinyl monomers including styrene by employing said composition, wherein the additive composition is not only suitable for substantial control and inhibition of polymerization of aromatic vinyl monomers including styrene, but also comprises reduced or minimized amounts of nitroxides (i.e. nitroxyls) and aromatic nitro compounds.

OBJECTS OF THE INVENTION

Accordingly, the main object of present invention is to provide an effective additive composition and method of its use, and method of its preparation, and method of controlling and inhibiting polymerization of aromatic vinyl monomers including styrene by employing said composition, wherein the additive composition is not only suitable for substantial control and inhibition of polymerization of aromatic vinyl monomers including styrene, but also comprises reduced or minimized amounts of nitroxides (i.e. nitroxyls) and aromatic nitro compounds.

This is also an object of present invention to provide an effective additive composition and method of its use, and method of its preparation and method of controlling and inhibiting polymerization of aromatic vinyl monomers including styrene by employing said composition, wherein the additive composition is not only suitable for substantial control and inhibition of polymerization of aromatic vinyl monomers including styrene, but is also required in relatively lower dosage as compared to dosage of prior art additives for achieving the same or better acceptable level of control and inhibition of polymerization of styrene.

This is also an object of present invention to provide an effective amine based additive composition and method of its use, and method of its preparation and method of controlling and inhibiting polymerization of aromatic vinyl monomers including styrene by employing said amine based additive composition, wherein the amine based additive composition is not only suitable for substantial control and inhibition of polymerization of aromatic vinyl monomers including styrene, but is also required in relatively lower dosage as compared to dosage of prior art additives for achieving the same or better acceptable level of control and inhibition of polymerization of styrene, and wherein the amine is selected from a group comprising:
  (i) hydroxyl alkyl tertiary amines,
  (ii) tertiary alkyl amines,
  (iii) hydroxyl alkyl primary amine; and
  (iv) mixture thereof.

The present invention particularly aims at providing an effective amine based additive composition and method of its use, and method of its preparation and method of controlling and inhibiting polymerization of aromatic vinyl monomers including styrene by employing said amine based additive composition, wherein the amine based additive composition is not only suitable for substantial control and inhibition of polymerization of aromatic vinyl monomers including styrene, but also comprises reduced or minimized amounts of nitroxides (i.e. nitroxyls) and aromatic nitro compounds, and is required in relatively lower dosage as compared to dosage of prior art additives for achieving the same or better acceptable level of control and inhibition of polymerization of aromatic vinyl monomers including styrene, and wherein the amine is selected from a group comprising:

(i) hydroxyl alkyl tertiary amines,
(ii) tertiary alkyl amines,
(iii) hydroxyl alkyl primary amine; and
(iv) mixture thereof, and therefore, the composition of present invention is not only economical, but is also environment friendly.

The present invention also aims at improving the performance of additive compositions comprising nitroxides (i.e. nitroxyls) and aromatic nitro compounds at higher temperature and in presence of air by further comprising one or more amines.

Other objects and advantages of present invention will become more apparent from the following description when read in conjunction with examples, which are not intended to limit scope of present invention.

DETAILED DESCRIPTION OF THE INVENTION

With aim to overcome above-described problems of prior art and to achieve above-described objects of the invention, the inventor has found that when an aliphatic amine, is added to composition comprising nitroxides (i.e. nitroxyls) and aromatic nitro compounds, then not only polymerization controlling and inhibiting efficiency of nitroxides and aromatic nitro compounds is substantially improved, but polymerization of aromatic vinyl monomers including styrene, surprisingly and unexpectedly, is also controlled and inhibited to the acceptable level at substantially reduced dosages of nitroxides and aromatic nitro compounds, substantially reduced dosages of the composition, and which makes the composition economical as well as environment friendly.

With aim to overcome above-described problems of prior art and to achieve above-described objects of the invention, the inventor has found that when an amine selected from a group comprising:

(i) hydroxyl alkyl tertiary amines,
(ii) tertiary alkyl amines,
(iii) hydroxyl alkyl primary amine; and
(iv) mixture thereof is added to composition comprising:
one or more of nitroxides (i.e. nitroxyls); and
one or more of aromatic nitro compounds, then not only polymerization controlling and inhibiting efficiency of nitroxides and aromatic nitro compounds is substantially improved, but polymerization of aromatic vinyl monomers including styrene, surprisingly and unexpectedly, is also controlled and inhibited to the acceptable level at substantially reduced dosages of nitroxides and aromatic nitro compounds, and at substantially reduced dosages of said composition comprising said amines which makes the composition economical as well as environment friendly.

Accordingly, the present invention relates to amine based additive composition to control and inhibition of polymerization of aromatic vinyl monomers including styrene comprising one or more of nitroxides (i.e. nitroxyls) and one or more of aromatic nitro compounds characterized in that it further comprises one or more aliphatic amines.

Accordingly, in particular, the present invention relates to amine based additive composition for controlling and inhibition of polymerization of aromatic vinyl monomers including styrene comprising:

(a) one or more of nitroxide (i.e. nitroxyl) compounds; and
(b) one or more of aromatic nitro compounds, characterized in that the said composition further comprises one or more of
(c) amines, wherein said amine is selected from a group comprising:
  (i) hydroxyl alkyl tertiary amines,
  (ii) tertiary alkyl amines,
  (iii) hydroxyl alkyl primary amine; and
  (iv) mixture thereof.

In accordance with present invention, the amine is an aliphatic tertiary amine, which contains one or more hydroxyl groups in the alkyl chain of the tertiary amine, preferably it contains three hydroxyl groups in the alkyl chain of the tertiary amine, more preferably the hydroxyl groups are hydroxyalkyl groups.

Accordingly, in accordance with most preferred embodiment of the present invention, the aliphatic tertiary amine containing three hydroxyl groups is tri-isopropanol amine or tris(2-hydroxypropyl)amine (TIPA).

In accordance with present invention, the hydroxyl alkyl tertiary amine is selected from a group consisting of tris(2-hydroxypropyl)amine (TIPA); N,N,N',N'-Tetrakis(2-hydroxypropyl) ethylene-diamine (Quadrol®); and N,N,N',N'-Tetrakis(2-hydroxyethyl) ethylene-diamine (THEED).

It may be noted that the Quadrol® may also be referred to as propoxylated ethylene diamine (PED) or Tetra(2-hydroxypropyl)ethylene-diamine and the one used in present invention includes as it as available from BASF under the tradename Quadrol 204®.

In accordance with one of the embodiments of the present invention, the tertiary alkyl amine is Tris[N-butylamine] (TBA).

In accordance with another embodiment of the present invention, the hydroxyl alkyl primary amine is monoethanolamine (MEA).

It has been found that when composition of present invention comprises one or more of above-described amines, the efficiency of nitroxides and aromatic nitro compounds to control and inhibit polymerization of aromatic vinyl monomers including styrene is, surprisingly and unexpectedly, substantially improved to the acceptable level that's too at substantially reduced dosages of nitroxides and aromatic nitro compounds, thereby making the composition of present invention relatively more economical and environment friendly.

In accordance with one of the embodiments of the present invention, the composition of present invention is added to the stream containing aromatic vinyl monomers including styrene in an amount varying from about 0.01 ppm to about 2000 ppm, preferably from about 1 ppm to about 2000 ppm by weight of the stream of monomer including styrene.

In accordance with one of the embodiments of the present invention, the nitroxide (i.e. nitroxyl) and aromatic nitro compounds are taken in a ratio varying from about 99:1 to about 1:99 by weight.

In accordance with one of the embodiments of the present invention, the composition comprises:

a) about 50 to about 99.5% by weight of I) mixture of said nitroxide (i.e. nitroxyl) compounds and said aromatic nitro compounds; and b) about 0.5 to about 50% by weight of II) said amines.

In accordance with one of the embodiments of the present invention, the nitroxide (or nitroxyl) compound is selected from the group comprising di-tert-butylnitroxyl, 1-oxyl-2,2, 6,6-tetramethylpiperidine, 1-oxyl-2,2,6,6-tetramethylpiperidin-4-ol, 1-oxyl-2,2,6,6-tetramethylpiperidin-4-one, and derivatives thereof; and di-nitroxides and derivatives comprising bis(1-oxyl-2,2,6,6-tetramethylpiperidin-4-yl)succinate, bis(1-oxyl-2,2,6,6-tetramethylpiperidin-4-yl)adipate, bis(1-oxyl-2,2,6,6-tetramethylpiperidin-4-yl)sebacate, and mixture thereof.

In accordance with one of the preferred embodiments of the present invention, the nitroxide (or nitroxyl) compound is selected from the group comprising bis(1-oxyl-2,2,6,6-tetramethylpiperidin-4-yl)sebacate and 1 oxyl-2,2,6,6, tetramethylpiperidin-4-ol or 4-hydroxy-2,2,6,6-tetramethylpiperidin-1-oxyl (or 4 Hydroxy Tempo or 4-HT), and mixture thereof.

In accordance with one of the preferred embodiments of the present invention, the nitroxide (or nitroxyl) compound is 1 oxyl-2,2,6,6, tetramethylpiperidin-4-ol (or 4 Hydroxy Tempo or 4-HT).

In accordance with one of the preferred embodiments of the present invention, the aromatic nitro compound contains a phenolic group or derivative thereof as well as the nitro group.

In accordance with one of the preferred embodiments of the present invention, the aromatic nitro compound is selected from a group comprising 4,6-dinitro-2-sec-butylphenol (DNBP) and 4,6-dinitro-ortho cresol or 4,6-dinitro-2-hydroxytoluene (DNOC), and mixture thereof.

In accordance with one of the preferred embodiments of the present invention, the aromatic nitro compound is 4,6-dinitro-2-sec-butylphenol (DNBP).

Accordingly, in another embodiment, the present invention also relates to method of using amine based additive composition of the present invention described herein, a reference to which is drawn in entirety, to control and inhibit polymerization of aromatic vinyl monomers including styrene, wherein the stream comprising aromatic vinyl monomer including styrene is treated with said composition comprising one or more of nitroxides (i.e. nitroxyls) and one or more of aromatic nitro compounds characterized in that it further comprises one or more of aliphatic amines.

In particular, in another embodiment, the present invention also relates to a method of using amine based additive composition of the present invention described herein, a reference to which is drawn in entirety, for controlling and inhibition of polymerization of aromatic vinyl monomers including styrene, wherein said composition comprises:

(a) one or more of nitroxide (i.e. nitroxyl) compounds; and (b) one or more of aromatic nitro compounds, characterized in that the said composition further comprises one or more of (c) amines, wherein said amine is selected from a group comprising:

(i) hydroxyl alkyl tertiary amines, (i) tertiary alkyl amines, (iii) hydroxyl alkyl primary amine; and (iv) mixture thereof, and said composition is added to monomer stream.

In accordance with one of the embodiments of the present invention, the method of using said amine based additive composition of the present invention comprises adding from about 0.01 ppm to about 2000 ppm, preferably from about 1 ppm to about 2000 ppm of said composition to the aromatic vinyl monomers stream including styrene based on weight of monomer.

It may be noted that all the features of the composition of the present invention described herein, a reference to which is drawn in entirety, are deemed to have been included in present method of using said amine based additive composition of the present invention.

Accordingly, in still another embodiment, the present invention also relates to method for controlling and inhibition polymerization of aromatic vinyl monomers including styrene by employing or adding amine based additive composition of the present invention described herein, a reference to which is drawn in entirety, to the aromatic vinyl monomers stream including styrene, wherein the stream comprising aromatic vinyl monomers including styrene is treated with a composition comprising one or more of nitroxides (i.e. nitroxyls) and one or more of aromatic nitro compounds characterized in that it further comprises one or more of aliphatic amines.

In particular, in another embodiment, the present invention also relates to a method for controlling and inhibition of polymerization of aromatic vinyl monomers including styrene by employing or adding amine based additive composition of the present invention described herein, a reference to which is drawn in entirety, to the aromatic vinyl monomers stream including styrene, wherein the stream comprising aromatic vinyl monomers including styrene is treated with said amine based additive composition comprising:

(a) one or more of nitroxide (i.e. nitroxyl) compounds; and (b) one or more of aromatic nitro compounds, characterized in that the said composition further comprises one or more of (c) amines, wherein said amine is selected from a group comprising:

(i) hydroxyl alkyl tertiary amines, (i) tertiary alkyl amines, (iii) hydroxyl alkyl primary amine; and (iv) mixture thereof.

In accordance with one of the embodiments of the present invention, the method for controlling and inhibition of polymerization by employing said amine based additive composition of the present invention comprises adding from about 0.01 ppm to about 2000 ppm, preferably from about 1 ppm to about 2000 ppm of said composition to the aromatic vinyl monomers stream including styrene based on weight of monomer.

It may be noted that all the features of the composition of the present invention described herein, a reference to which is drawn in entirety, are deemed to have been included in present method for controlling and inhibition of polymerization by employing said amine based additive composition of the present invention.

In accordance with one of the embodiments of the present invention, the composition of present invention may be mixed with stream containing aromatic vinyl monomers either before the stream enters into processing system or after the stream has entered into processing system, but preferably the composition is added to the stream containing aromatic vinyl monomers before its processing starts so that polymerization of aromatic vinyl monomers is avoided.

In accordance with one of the embodiments of the present invention, the present composition may be used over a wide range of temperature including 50 degree C. to 180 degree C., preferably over the range of 60 degree C. to 180 degree C.

The composition of present invention may be prepared in any known manner to prepare the compositions.

Accordingly, in still another embodiment, the present invention also relates to method of preparing amine based additive composition of the present invention described herein, a reference to which is drawn in entirety, for controlling and inhibiting polymerization of aromatic vinyl monomers including styrene, wherein one or more of nitroxide and one or more of aromatic nitro compounds are mixed first, and then, one or more of said amines are added to the mixture of said nitroxide and aromatic nitro compounds.

In particular, in still another embodiment, the present invention also relates to a method for preparing amine based additive composition of the present invention described herein, a reference to which is drawn in entirety, for controlling and inhibiting polymerization of aromatic vinyl monomers including styrene, wherein the method comprises:

(A) mixing one or more of said nitroxide (i.e. nitroxyl) compounds and one or more of said aromatic nitro compounds, characterized in that the said mixture of said nitroxide (i.e. nitroxyl) compounds and said aromatic nitro compounds is further mixed with one or more of (B) said amines, wherein said amine is selected from a group comprising:
(i) hydroxyl alkyl tertiary amines,
(i) tertiary alkyl amines,
(iii) hydroxyl alkyl primary amine; and
(iv) mixture thereof.

In another embodiment, the composition of present invention is prepared by mixing one or more of nitroxide compounds, one or more of aromatic nitro compounds, and one or more of said amines individually or in any possible combination.

It may be noted that all the features of the composition of the present invention described herein, a reference to which is drawn in entirety, are deemed to have been included in present method for preparing said amine based additive composition of the present invention.

In one of the embodiments, the inventor has found that when any one of the triethanolamine (TEA), N,N,disec-butyl-para-phenylene diamine (UOP5), ethylene diamine (EDA), tetraethylenepentamine (TEPA), dibutyl amine (DBA), octyle amine, dipropyl amine (DPA), or diethanol amine (DEA) amines is added to prior art additive composition comprising DNBP and 4HT, then, surprisingly and unexpectedly, these amines result in substantial reduction in efficiency of prior art additive composition consisting to control and inhibit polymerization of styrene for all concentrations of the prior art additive. Therefore, as per present invention the TEA, EDA, TEPA, UOP5, DBA, Octyle Amine, DEA, are not the selected amines/additives, or the present composition does not comprise any of these amines.

EXAMPLES

The present invention is now described with the help of following examples, which are not intended to limit scope of the present invention, but have been incorporated to illustrate mode and best mode of performing the present invention.

EXPERIMENTS

Main Experiment

In the following experiments, weighed amount of distilled styrene and additives are taken in a reactor (tube reactor or round bottom reactor) equipped with thermometer and nitrogen or air inlet and outlet. Enough $N_2$ or air flow is maintained to ensure proper agitation. The contents of the reactor are heated to selected temperature (120° C. or 135° C.) under continuous nitrogen or air flow for selected duration (for about 2 hrs.). After that selected duration, the reactor is cooled to below 10° C. by immersing in crushed ice. The contents of the reactor are then poured into a beaker containing methanol (methanol precipitation). The precipitate obtained is filtered, dried to remove methanol and weighed. Approximately, for about 1.5-2 g chilled polymerization mixture, about 80 g methanol was used to precipitate the polymer formed in the styrene solution. The weight of the precipitate is reported as % polymer formed in following tables.

It may be noted that styrene was purified before use to remove the stabilizers.

In following examples, the prior art additive composition is a composition comprising aromatic nitro compound and nitroxide compound, wherein aromatic nitro compound is 4,6-dinitro-2-sec-butylphenol (DNBP); and nitroxide compound is 1 oxyl-2,2,6,6, tetramethylpiperidin-4-ol (or 4 Hydroxy Tempo or 4-HT), which are taken in an amount of about 100, 200, 300, 400, 500, 1000 ppm in various weight ratios of 90:10 [referred as DNBP:4HT (90:10)], 80:20 [referred as DNBP:4HT (80:20)], 70:30 [referred as DNBP:4HT (70:30)], 50:50 [referred as DNBP:4HT (50:50)], 30:70 [referred as DNBP:4HT (30:70)], and 20:80 [referred as DNBP:4HT (20:80)].

In following examples, the present additive composition is a composition comprising 4,6-dinitro-2-sec-butylphenol (DNBP) being aromatic nitro compound; 1 oxyl-2,2,6,6, tetramethylpiperidin-4-ol (or 4 Hydroxy Tempo or 4-HT) being nitroxide (DNBP and 4HT); and additionally comprising TIPA, Quadrol, THEED, TBA, or MEA being amine of the present invention.

The inventor has further compared the results of present compositions with additive compositions comprising (DNBP and 4HT), and triethanolamine (TEA), N,N,disec-butyl-para-phenylene diamine (UOP5), ethylene diamine (EDA), tetraethylenepentamine (TEPA), dibutyl amine (DBA), octyle amine, dipropyl amine (DPA), or diethanol amine (DEA) for comparative purposes.

In following examples, from about 1 to about 25 ppm of amine of the present invention and of amine for the comparative purpose is added to about 100, 200, 300, 400, 500, 1000 ppm of above-said mixture of nitroxide and aromatic nitro compounds, wherein said mixture of nitroxide and aromatic nitro compounds is taken in weight ratios of 90:10, 80:20, 70:30, 50:50, 30:70 and 20:80.

Experiment 1

The results of above Main Experiment when performed in a tube reactor with 10 g of distilled styrene for heating to 120° C. for 2 h are provided in Table I for 100 ppm dosage and in Table II for 200, 300 and 400 ppm dosages of mixture of nitroxide and aromatic nitro compounds taken in weight ratios of 90:10, 80:20, 70:30, 50:50, 30:70 and 20:80, wherein 1 to 25 ppm of amine of the present invention and of amine for the comparative purpose has been added.

TABLE I

Present Additive Composition comprising (DNBP and 4HT), and TIPA, Quadrol, THEED, TBA, or MEA Vs. prior art additive composition consisting of DNBP and 4HT; and Vs. Comparative Additive Composition comprising (DNBP and 4HT), and DPA, TEA, EDA, TEPA, UOP5, DBA, Octyl Amine or DEA (for comparative purposes).

| Dosage, Active (ppm) | DNBP:4HT (90:10) | DNBP:4HT (80:20) | DNBP:4HT (70:30) | DNBP:4HT (50:50) | DNBP:4HT (30:70) | DNBP:4HT (20:80) |
|---|---|---|---|---|---|---|
| 100 (Prior Art, DNBP and 4HT) | 2.50 | 2.15 | 1.81 | 1.6 | 2.5 | 4.19 |
| 100 + 1 (TIPA) | 1.20 | 0.97 | 1.16 | 0.56 | 0.61 | 0.72 |
| 100 + 2 (TIPA) | 1.03 | 0.87 | 1.07 | 0.43 | 0.44 | 0.63 |
| 100 + 5 (TIPA) | 0.86 | 0.76 | 0.70 | 0.25 | 0.29 | 0.45 |
| 100 + 10 (TIPA) | 0.72 | 0.62 | 0.60 | 0.20 | 0.27 | 0.40 |
| 100 + 20 (TIPA) | 0.80 | 0.72 | 0.75 | 0.22 | 0.39 | 0.58 |
| 100 + 25 (TIPA) | 0.98 | 0.87 | 0.89 | 0.32 | 0.42 | 0.70 |
| 100 + 5 (Quadrol) | 1.52 | 1.28 | 1.03 | 0.93 | 1.64 | 2.25 |
| 100 + 10 (Quadrol) | 1.42 | 1.18 | 0.90 | 0.81 | 1.49 | 2.01 |
| 100 + 20 (Quadrol) | 1.55 | 1.25 | 1.05 | 0.92 | 1.75 | 2.15 |
| 100 + 25 (Quadrol) | 1.82 | 1.40 | 1.21 | 1.05 | 1.85 | 2.35 |
| 100 + 5 (THEED) | 1.57 | 1.35 | 1.0 | 0.98 | 1.69 | 2.20 |
| 100 + 10 (THEED) | 1.40 | 1.16 | 0.93 | 0.82 | 1.55 | 2.05 |
| 100 + 20 (THEED) | 1.58 | 1.22 | 1.10 | 0.95 | 1.71 | 2.10 |
| 100 + 25 (THEED) | 1.80 | 1.35 | 1.15 | 1.10 | 1.80 | 2.30 |
| 100 + 5 (TBA) | 2.0 | 1.70 | 1.41 | 1.12 | 1.92 | 3.84 |
| 100 + 10 (TBA) | 1.81 | 1.45 | 1.36 | 1.0 | 1.72 | 3.52 |
| 100 + 20 (TBA) | 2.11 | 1.94 | 1.71 | 1.53 | 2.03 | 3.73 |
| 100 + 25 (TBA) | 2.24 | 1.93 | 1.84 | 1.63 | 2.22 | 3.93 |
| 100 + 5 (MEA) | 2.48 | 2.15 | 1.95 | 1.65 | 2.48 | 4.02 |
| 100 +10 (MEA) | 2.51 | 2.08 | 1.89 | 1.74 | 2.55 | 4.15 |
| 100 + 20 (MEA) | 2.46 | 2.09 | 2.0 | 1.77 | 2.61 | 4.21 |
| 100 + 25 (MEA) | 2.58 | 2.21 | 1.98 | 1.80 | 2.59 | 4.20 |
| 100 + 5 (DPA) | 2.40 | 2.03 | 1.65 | 1.40 | 2.33 | 3.95 |
| 100 + 10 (DPA) | 2.44 | 2.01 | 1.64 | 1.48 | 2.37 | 4.06 |
| 100 + 20 (DPA) | 2.55 | 2.22 | 1.92 | 1.71 | 2.55 | 4.28 |
| 100 + 25 (DPA) | 2.51 | 2.25 | 1.96 | 1.79 | 2.62 | 4.29 |
| 100 + 5 (TEA) | 2.64 | 2.33 | 2.0 | 1.93 | 2.95 | 4.43 |
| 100 +10 (TEA) | 2.74 | 2.5 | 2.23 | 2.0 | 3.26 | 4.37 |
| 100 + 20 (TEA) | 2.82 | 2.55 | 2.33 | 2.16 | 3.36 | 4.53 |
| 100 + 25 (TEA) | 2.96 | 2.67 | 2.55 | 2.27 | 3.54 | 4.63 |
| 100 + 5 (EDA) | 2.60 | 2.22 | 2.03 | 1.84 | 2.70 | 4.23 |
| 100 + 10 (EDA) | 2.66 | 2.21 | 2.05 | 1.90 | 2.75 | 4.31 |
| 100 + 20 (EDA) | 2.62 | 2.28 | 2.15 | 1.96 | 2.56 | 4.32 |
| 100 + 25 (EDA) | 2.71 | 2.35 | 2.25 | 2.05 | 2.89 | 4.44 |
| 100 + 5 (TEPA) | 2.66 | 2.21 | 2.0 | 1.89 | 2.75 | 4.39 |
| 100 + 10 (TEPA) | 2.69 | 2.25 | 2.08 | 1.92 | 2.70 | 4.35 |
| 100 + 20 (TEPA) | 2.70 | 2.34 | 2.15 | 1.95 | 2.85 | 4.41 |
| 100 + 25 (TEPA) | 2.75 | 2.31 | 2.20 | 1.89 | 2.95 | 4.43 |
| 100 + 5 (UOP5) | 2.70 | 2.26 | 2.06 | 1.88 | 2.76 | 4.39 |
| 100 + 10 (UOP5) | 2.68 | 2.23 | 2.08 | 1.92 | 2.80 | 4.36 |
| 100 + 20 (UOP5) | 2.60 | 2.58 | 2.11 | 2.05 | 2.82 | 4.45 |
| 100 + 25 (UOP5) | 2.63 | 2.78 | 2.20 | 2.11 | 2.80 | 4.52 |
| 100 + 5 (DBA) | 2.58 | 2.18 | 2.10 | 1.95 | 2.88 | 4.20 |
| 100 + 10 (DBA) | 2.65 | 2.25 | 2.11 | 1.90 | 2.95 | 4.20 |
| 100 + 20 (DBA) | 2.75 | 2.30 | 2.16 | 2.05 | 2.92 | 4.25 |
| 100 + 25 (DBA) | 2.85 | 2.33 | 2.25 | 2.15 | 3.0 | 4.32 |
| 100 + 5 (Octyl amine) | 2.48 | 2.19 | 2.02 | 1.86 | 2.83 | 4.05 |
| 100 + 10 (Octyl amine) | 2.44 | 2.21 | 2.05 | 1.90 | 2.79 | 4.02 |
| 100 + 20 (Octyl amine) | 2.70 | 2.25 | 2.09 | 1.99 | 2.81 | 4.15 |
| 100 + 25 (Octyl amine) | 2.78 | 2.16 | 2.10 | 2.11 | 2.86 | 4.27 |
| 100 + 5 (DEA) | 2.55 | 2.2 | 2.07 | 1.90 | 2.65 | 4.23 |
| 100 + 10 (DEA) | 2.60 | 2.22 | 2.10 | 1.95 | 2.75 | 4.33 |
| 100 + 20 (DEA) | 2.66 | 2.26 | 2.10 | 1.99 | 2.82 | 4.36 |
| 100 + 25 (DEA) | 2.68 | 2.33 | 2.15 | 2.10 | 2.90 | 4.40 |

In Table I, 100 ppm is active dosage of DNBP and 4HT in various given ratios of 90:10, 80:20, 70:30, 50:50, 30:70 and 20:80, and 1, 2, 5, 10, 20 and 25 ppm of the selected amine is added to that 100 ppm of mixture of DNBP and 4HT.

TABLE II

Present Additive Composition comprising (DNBP and 4HT), and TIPA, Quadrol, THEED, TBA, or MEA Vs. prior art additive consisting of DNBP and 4HT; and Vs. Comparative Additive Composition comprising (DNBP and 4HT), and DPA, TEA, EDA, TEPA, UOP5, DBA, Octyl Amine or DEA (for comparative purposes).

| Dosage Active (ppm) | DNBP + 4HT** | DNBP and 4HT in 90:10 ratio and third Amine is | | | | | | | | | | | | |
|---|---|---|---|---|---|---|---|---|---|---|---|---|---|---|
| | | TIPA | Quadrol | THEED | TBA | TEA | DPA | EDA | TEPA | UOP5 | DBA | MEA | DEA | Octyl amine |
| 200 + 10 ppm* | 1.10 | 0.15 | 0.31 | 0.35 | 1.10 | 1.16 | 1.14 | 1.12 | 1.10 | 1.13 | 1.15 | 0.92 | 1.15 | 1.12 |
| 300 + 15 ppm* | 0.22 | 0 | 0 | 0 | 0.25 | 0.27 | 0.30 | 0.25 | 0.28 | 0.25 | 0.31 | 0.11 | 0.28 | 0.26 |
| 400 + 20 ppm* | 0.1 | 0 | 0 | 0 | 0.14 | 0.18 | 0.18 | 0.15 | 0.15 | 0.17 | 0.18 | 0 | 0.15 | 0.18 |

In Table II, 200, 300 and 400 ppm is active dosage of DNBP and 4HT in ratio of 90:10, and 10, 15 and 20 ppm of the selected amine is added to that 200, 300 and 400 ppm of mixture of DNBP and 4HT.

The above experimental data confirms the synergistic effect, and the surprising and unexpected technical effects and advantages of the additive composition of the present invention which comprises DNBP, 4HT and TIPA; DNBP, 4HT and Quadrol; DNBP, 4HT and THEED; DNBP, 4HT and TBA; and DNBP, 4HT and MEA.

As can be seen from above data, with addition of about 1 to about 25 ppm of TIPA, Quadrol, THEED or TBA in about 100 ppm mixture of DNBP and 4HT respectively taken in 90:10, 80:20, 70:30, 50:50, 30:70 and 20:80 weight ratios, the efficiency of prior art additive composition consisting of DNBP and 4HT to control and inhibit polymerization of styrene is, surprisingly and unexpectedly, generally improved.

As can be seen, the improvement of efficiency of the prior art additive when TIPA or Quadrol or THEED or TBA is added is generally substantial for all concentrations. However, the improvement of efficiency for Quadrol or THEED or TBA is not as substantial as for TIPA, and for TBA is not as substantial as for Quadrol or THEED. Therefore, as per present invention, TIPA is the most preferred amine/additive, and Quadrol and THEED are the preferred amines/additives, and TBA is one of the selected amines/additives.

It may be noted that, surprisingly and unexpectedly, with increase in concentration of TIPA or Quadrol or THEED or TBA, i.e. when about 20 ppm or more of TIPA or Quadrol or THEED or TBA is added to mixture of DNBP and 4HT, the polymerization inhibition efficiency of present additive composition reduces, the reasons for which are not know at present.

As can be seen from above data, surprisingly and unexpectedly, the additive composition comprising 100 μm of mixture of DNBP and 4HT; and 5, 10, 20 and 25 ppm of MEA is generally not effective. However, the additive composition comprising 200, 300 and 400 μm of mixture of DNBP and 4HT; and respectively 10, 15 and 20 ppm of MEA is generally very effective. Therefore, as per present invention, MEA is one of the preferred choices when higher amounts mixture of DNBP and 4HT are employed.

As can be seen from above data, the additive composition comprising DNBP, 4HT and DPA results in only marginal improvement of the efficiency of prior art additive composition consisting of DNBP and 4HT to control and inhibit polymerization of styrene. Therefore, as per present invention, DPA is not the selected amine/additive.

As can be seen from above data, the comparative amines including TEA, EDA, TEPA, UOP5, DBA, Octyle Amine, DEA, surprisingly and unexpectedly, result in substantial reduction in efficiency of prior art additive composition consisting of DNBP and 4HT to control and inhibit polymerization of styrene for all concentrations of the prior art additive. Therefore, as per present invention the TEA, EDA, TEPA, UOP5, DBA, Octyle Amine, DEA, are not the selected amines/additives, or the present composition does not comprise any of these amines.

Accordingly, in view of above experimental data and analysis thereof, it can be concluded that only the additive compositions of the present invention comprising DNBP, 4HT and TIPA; DNBP, 4HT and Quadrol; DNBP, 4HT and THEED; DNBP, 4HT and TBA; and DNBP, 4HT and MEA, surprisingly and unexpectedly, result in improvement of control and polymerization inhibition efficiency of prior art additive composition consisting of DNBP and 4HT, and these findings confirm synergistic effect of present compositions.

Experiment 2

In view of above unexpected advantages of additive composition of present invention, further experiments of above Main Experiment were performed in a tube reactor with 10 g of distilled styrene for heating to 135° C. for 2 h under continuous flow of nitrogen, and results thereof are provided in Table III.

TABLE III

| Active Dosage (ppm) | DNBP:4HT (90:10) | DNBP:4HT (80:20) | DNBP:4HT (70:30) |
|---|---|---|---|
| 500 | 6.51 | 5.52 | 5.29 |
| 1000 | 3.11 | 2.64 | 2.02 |
| 500 + 5 TIPA | 3.50 | 3.04 | 2.48 |
| 500 + 10 TIPA | 3.21 | 2.81 | 2.24 |
| 500 + 15 TIPA | 3.09 | 2.67 | 2.11 |
| 500 + 20 TIPA | 3.01 | 2.60 | 1.98 |

It can be seen from Table III that present composition comprising (DNBP and 4HT) and TIPA is effective and efficient even at higher dosage and higher temperature. The present composition comprising 500 ppm of mixture of DNBP and 4HT in 90:10, 80:20 and 70:30 ratios with just 15 ppm of TIPA (2.91% of the total composition) has same efficiency to control and inhibit polymerization of styrene as 1000 ppm of prior art composition without TIPA, which confirms that present composition is capable of achieving same efficiency to control and inhibit polymerization of styrene with half of the dosage of the prior art composition, and thereby, resulting in economical and environmental benefits.

It can also be seen from Table III that polymerization of styrene is substantially reduced just on addition of 5 ppm (0.99% of total composition), 10 ppm (1.96% of total composition), 15 ppm (2.91% of total composition) or 20 ppm (3.85% of total composition) of TIPA in 500 ppm of prior art additive composition consisting of DNBP and 4HT.

It can also been seen from above Table III that just with addition of 0.99% to 3.85% of TIPA of total composition, the present invention comprising DNBP, 4HT and TIPA demonstrates successive increase in efficiency of prior art additive composition to control and inhibit polymerization of styrene, i.e. % polymerization successively reduces from 3.50% to 3.01% for 90:10 ratio of DNBP and 4HT, from 3.04% to 2.60% for 80:20 ratio of DNBP and 4HT, and from 2.48% to 1.98% for 70:30 ratio of DNBP and 4HT.

It can also be seen from Table III that there is about 1.82 to 2.67 times reduction in polymer formation when present composition comprises DNBP and 4HT, and just about 1 or 2 ppm of TIPA as compared to prior art additive composition which also confirms synergistic effect of present composition.

These findings also confirm synergistic effect of present composition.

Experiment 3

The results of above Main Experiment when performed in a tube reactor with 10 g of distilled styrene for heating to 135° C. for 2 h under air are provided in Table IV.

TABLE IV

| Active Dosage (ppm) | DNBP:4HT (90:10) | DNBP:4HT (80:20) | DNBP:4HT (70:30) |
|---|---|---|---|
| 500 | 9.74 | 3.91 | 3.13 |
| 500 + 5 Activator | 3.2 | 1.82 | 1.01 |
| 500 + 10 Activator | 2.91 | 1.53 | 0.85 |
| 500 + 15 Activator | 2.71 | 1.21 | 0.62 |
| 500 + 20 Activator | 2.63 | 1.10 | 0.53 |

It can be seen from Table IV that present composition is effective and efficient even at higher dosage, higher temperature and under air, and trend of data in Table III is maintained.

It can also be seen from Table IV that polymerization of styrene is substantially reduced just on addition of 5 ppm (0.99% of total composition), 10 ppm (1.96% of total composition), 15 ppm (2.91% of total composition) or 20 ppm (3.85% of total composition) of TIPA in 500 ppm of prior art additive composition.

It can also be seen from above Table IV that just with addition of 0.99% to 3.85% of TIPA of total composition, the present invention comprising DNBP, 4HT and TIPA demonstrates successive increase in efficiency of prior art additive composition to control and inhibit polymerization of styrene, i.e. % polymerization successively reduces from 3.2% to 2.63% for 90:10 ratio of DNBP and 4HT, from 1.82% to 1.10% for 80:20 ratio of DNBP and 4HT, and from 1.10% to 0.53% for 70:30 ratio of DNBP and 4HT.

It can also be seen from Table IV that there is about 2.15 to 5.9 times reduction in polymer formation when present composition comprises DNBP and 4HT, and just about 1 or 2 ppm of TIPA as compared to prior art additive composition, which also confirms synergistic effect of present composition.

These findings also confirm synergistic effect of present composition, and that present composition is capable of achieving far better efficiency to control and inhibit polymerization of styrene with same dosage of the prior art composition, and thereby, resulting in economical and environmental benefits.

Experiment 4

The results of above Main Experiment when performed in a round bottom reactor with 100 g of distilled styrene, and reactor being provided with mechanical stirrer to have continuous flow of nitrogen under stirring, for heating to 120° C. for 2 h are provided in Table V. In this experiment, after 2 h, when reactor is cooled, a small portion of the mixture is taken in a test tube and cooled to below 10° C. On confirmation of above unexpected results this experiment was carried out only for 90:10 and 80:20 ratios of DNBP and 4HT.

TABLE V

| Active Dosage (ppm) | DNBP:4HT (90:10) | DNBP:4HT (80:20) |
|---|---|---|
| 100 (Prior Art) | 13.08 | 11.21 |
| 100 + 1 TIPA | 3.62 | 3.52 |
| 100 + 2 TIPA | 3.41 | 2.82 |
| 100 + 8 TIPA | 2.8 | |
| 100 + 10 TIPA | 2.6 | |

It is understood from above Table V that when just 1 ppm, 2 ppm, 8 ppm or 10 ppm of TIPA is added to 100 ppm of prior art composition consisting of DNBP and 4HT in 90:10 or 80:20 ratio of DNBP and 4HT, the efficiency of prior art additive composition to control and inhibit polymerization of styrene is, surprisingly and unexpectedly, improved substantially.

It can be seen from Table V that polymerization of styrene is substantially reduced just on addition of 1, 2, 8 or 10 ppm of TIPA in 100 ppm of prior art additive composition which confirms synergistic effect of present composition.

It can also be seen from Table V that there is about 3.18 to 5.03 times reduction in polymer formation when present composition comprises DNBP and 4HT, and just about 1 or 2 ppm of TIPA as compared to prior art additive composition which also confirms synergistic effect of present composition.

It can also be seen from the above Table V that increasing the dosage of TIPA to the prior art additive successively reduces the polymerization of styrene.

Experiment 5

The results of above Main Experiment when performed in a round bottom reactor with 100 g of distilled styrene, and reactor being provided with mechanical stirrer, for heating to 120° C. for 2 h are provided in Table VI. In this experiment, after 2 h, when reactor is cooled, a small portion of the mixture is taken in a test tube and cooled to below 10° C. Further, the $N_2$ is purged through the system for 10 mins, and thereafter, the polymerization is carried out without any gas flow and under stirring.

TABLE VI

| Active Dosage (ppm) | DNBP:4HT (90:10) | DNBP:4HT (80:20) | DNBP:4HT (70:30) | DNBP:4HT (50:50) |
|---|---|---|---|---|
| 200 (Prior Art) | 3.9 | 2.65 | 2.30 | 0.83 |
| 100 + 1 TIPA | 4.5 | 2.95 | 1.51 | 1.02 |
| 100 + 2 TIPA | 4.22 | 2.88 | 1.24 | 0.81 |
| 100 + 4 TIPA | 4.0 | 2.62 | | |

It can be seen from Table VI that present composition comprising 100 ppm of mixture of DNBP and 4HT in 90:10 and 80:20 ratios with just 4 ppm of TIPA (3.8% of the total composition) has same efficiency to control and inhibit polymerization of styrene as 200 ppm of prior art composition without TIPA, which confirms that present composition is capable of achieving same efficiency to control and inhibit polymerization of styrene with half of the dosage of the prior art composition thereby resulting in economical and environmental benefits.

Similarly, present composition comprising 100 ppm of mixture of DNBP and 4HT in 80:20 ratio with just 2 ppm of TIPA (1.96% of the total composition) has same efficiency to control and inhibit polymerization of styrene as 200 ppm of prior art composition without TIPA.

Unexpectedly, present composition comprising 100 ppm of mixture of DNBP and 4HT in 70:30 ratio with just 1 ppm of TIPA (0.99% of the total composition) or 2 ppm of TIPA (1.96% of the total composition) has far better efficiency to control and inhibit polymerization of styrene than 200 ppm (double the dosage of present composition) of prior art composition without TIPA.

It is also understood from above Table VI that when just 1 ppm, 2 ppm, or 4 ppm of TIPA is added to 100 ppm of prior art composition consisting of DNBP and 4HT in 90:10 or 80:20 ratio of DNBP and 4HT, the efficiency of prior art additive composition to control and inhibit polymerization of styrene is, surprisingly and unexpectedly, successively improved, i.e. % polymerization reduces from 4.5% to 4.0% or from 2.95% to 2.62%.

These findings also confirm synergistic effect of present composition.

Above experimental results confirm that presently provided composition is far superior than prior art composition, and hence, has technical advantages and surprising effects over the prior art additive composition.

It may be noted that the term "about" as employed herein is not intended to enlarge scope of claimed invention, but has been incorporated only to include experimental errors permissible in the field of the art.

The invention claimed is:

1. Amine based additive composition for controlling and inhibition of polymerization of aromatic vinyl monomers including styrene comprising:
   (a) one or more of nitroxide (i.e. nitroxyl) compounds; and
   (b) one or more of aromatic nitro compounds,
characterized in that the said composition further comprises one or more of
   (c) amines,
wherein said amines comprise:
   (i) hydroxyl alkyl tertiary amines comprising tris(2-hydroxypropyl)amine (TIPA); N,N,N',N'-Tetrakis (2-hydroxypropyl) ethylene-diamine (Quadrol); N,N,N',N'-Tetrakis (2-hydroxyethyl) ethylene-diamine (THEED), or a mixture thereof.

2. The additive composition as claimed in claim 1, wherein said amines further comprise:
   i) a hydroxyl alkyl primary amine which is monoethanolamine (MEA) in combination with the hydroxyl alkyl tertiary amines;
   (ii) tertiary alkyl amines in combination with the hydroxyl alkyl tertiary amines;
   (iii) the hydroxyl alkyl primary amine and the tertiary alkyl amines in combination with the hydroxyl alkyl tertiary amines; or
   (iv) a mixture thereof.

3. Amine based additive composition for controlling and inhibition of polymerization of aromatic vinyl monomers including styrene comprising:
   (a) one or more of nitroxide (i.e. nitroxyl) compounds; and
   (b) one or more of aromatic nitro compounds,
characterized in that the said composition further comprises one or more of
   (c) amines,
wherein said amines comprise:
   a tertiary alkyl amine which is Tris[N-butylamine] (TBA).

4. The additive composition as claimed in claim 3, wherein said amines further comprise:
   (i) a hydroxyl alkyl primary amine which is monoethanolamine (MEA) in combination with the tertiary alkyl amine;
   (ii) hydroxyl alkyl tertiary amines in combination with the tertiary alkyl amine;
   (iii) the hydroxyl alkyl primary amine and the hydroxyl alkyl tertiary amines in combination with the tertiary alkyl amine; or
   (iv) a mixture thereof.

5. The additive composition as claimed in claim 1, wherein said nitroxide (i.e. nitroxyl) and said aromatic nitro compounds are taken in a ratio varying from about 99:1 to about 1:99 by weight.

6. The additive composition as claimed in claim 1, wherein said composition comprises:
   a) about 50 to about 99.5% by weight of I) mixture of said nitroxide (i.e. nitroxyl) compounds and said aromatic nitro compounds; and
   b) about 0.5 to about 50% by weight of II) said amines.

7. The additive composition as claimed in claim 1, wherein about 0.01 to about 2000 ppm of said composition is added to aromatic vinyl monomers stream based on weight of monomer.

8. The additive composition as claimed in claim 1, wherein said nitroxide (i.e. nitroxyl) compound comprises di-tert-butylnitroxyl, 1-oxyl-2,2,6,6-tetramethylpiperidine, 1-oxyl-2,2,6,6-tetramethylpiperidin-4-ol, 1-oxyl-2,2,6,6-tetramethylpiperidin-4-one, or derivatives thereof; or di-nitroxides or derivatives comprising bis(1-oxyl-2,2,6,6-tetramethylpiperidin-4-yl)sebacate, bis(1-oxyl-2,2,6,6-tetramethylpiperidin-4-yl)succinate, bis(1-oxyl-2,2,6,6-tetramethylpiperidin-4-yl)adipate, or a mixture thereof.

9. The additive composition as claimed in claim 1, wherein said nitroxide (i.e. nitroxyl) compound comprises bis(1-oxyl-2,2,6,6-tetramethylpiperidin-4-yl)sebacate, 1 oxyl-2,2,6,6, tetramethylpiperidin-4-ol, 4-hydroxy-2,2,6,6-tetramethylpiperidin-1-oxyl (or 4 Hydroxy Tempo or 4-HT), or a mixture thereof.

10. The additive composition as claimed in claim 1, wherein said nitroxide (i.e. nitroxyl) compound is 1 oxyl-2, 2,6,6, tetramethylpiperidin-4-ol (or 4 Hydroxy Tempo or 4-HIT).

11. The additive composition as claimed in claim 1, wherein said aromatic nitro compound contains a phenolic group or derivative thereof as well as the nitro group.

12. The additive composition as claimed in claim 1, wherein said aromatic nitro compound comprises 4,6-dinitro-2-sec-butylphenol (DNBP), 4,6-dinitro-ortho cresol, 4,6-dinitro-2-hydroxytoluene (DNOC), or a mixture thereof.

13. The additive composition as claimed in claim 1, wherein said aromatic nitro compound is 4,6-dinitro-2-sec-butylphenol (DNBP).

14. The additive composition as claimed in claim 1, wherein said composition does not comprise triethanolamine (TEA), N,N,disec-butyl-para-phenylene diamine (UOP5), ethylene diamine (EDA), tetraethylenepentamine (TEPA), dibutyl amine (DBA), octyle amine, dipropyl amine (DPA), and diethanol amine (DEA).

15. A method for controlling and inhibition of polymerization of aromatic vinyl monomers including styrene by adding amine based additive composition as claimed in claim 1 to monomer stream, wherein said composition comprises:

(a) one or more of nitroxide (i.e. nitroxyl) compounds; and
(b) one or more of aromatic nitro compounds, characterized in that the said composition further comprises one or more of (c) amines, wherein said amines comprise:
(i) hydroxyl alkyl tertiary amines comprising tris(2-hydroxypropyl)amine (TIPA); N,N,N',N'-Tetrakis (2-hydroxypropyl) ethylene-diamine (Quadrol); N,N,N',N'-Tetrakis (2-hydroxyethyl) ethylene-diamine (THEED), or a mixture thereof.

16. The method as claimed in claim 15, wherein about 0.01 to about 2000 ppm of said composition is added to aromatic vinyl monomers stream based on weight of monomer.

17. A method of using amine based additive composition as claimed in claim 1 for controlling and inhibition of polymerization of aromatic vinyl monomers including styrene, wherein said composition comprises:

(a) one or more of nitroxide (i.e. nitroxyl) compounds; and
(b) one or more of aromatic nitro compounds, characterized in that the said composition further comprises one or more of (c) amines, wherein said amines comprise:
(i) hydroxyl alkyl tertiary amines comprising tris(2-hydroxypropyl)amine (TIPA); N,N,N',N'-Tetrakis (2-hydroxypropyl) ethylene-diamine (Quadrol); N,N,N',N'-Tetrakis (2-hydroxyethyl) ethylene-diamine (THEED), or a mixture thereof, and said composition is added to monomer stream.

18. The method as claimed in claim 17, wherein about 0.01 to about 2000 ppm of said composition is added to aromatic vinyl monomers stream based on weight of monomer.

19. A method for preparing amine based additive composition as claimed in claim 1 for controlling and inhibiting polymerization of aromatic vinyl monomers including styrene, wherein the method comprises:

(A) mixing one or more of said nitroxide (i.e. nitroxyl) compounds and one or more of said aromatic nitro compounds, characterized in that said mixture of said nitroxide (i.e. nitroxyl) compounds and said aromatic nitro compounds is further mixed with one or more of (B) said amines, wherein said amines comprise:
(i) hydroxyl alkyl tertiary amines comprising tris(2-hydroxypropyl)amine (TIPA); N,N,N',N'-Tetrakis (2-hydroxypropyl) ethylene-diamine (Quadrol); N,N,N',N'-Tetrakis (2-hydroxyethyl) ethylene-diamine (THEED), or a mixture thereof.

20. The method as claimed in claim 19, wherein said one or more of nitroxide compounds, said one or more of aromatic nitro compounds, and said one or more amines are mixed individually.

* * * * *

UNITED STATES PATENT AND TRADEMARK OFFICE
CERTIFICATE OF CORRECTION

PATENT NO. : 9,334,445 B2
APPLICATION NO. : 14/361220
DATED : May 10, 2016
INVENTOR(S) : Mahesh Subramaniyam Page 1 of 1

It is certified that error appears in the above-identified patent and that said Letters Patent is hereby corrected as shown below:

In the Claims:

Claim 10, col. 16, line 46, replace "4-HIT)." with --4-HT).--.

Signed and Sealed this
Fifth Day of July, 2016

Michelle K. Lee
*Director of the United States Patent and Trademark Office*